United States Patent
Holmström et al.

[11] Patent Number: 5,728,281
[45] Date of Patent: Mar. 17, 1998

[54] IMPLANTABLE MEDICAL DEVICE INCLUDING AN ARRANGEMENT FOR MEASURING A BLOOD PROPERTY HAVING A CARBON REFERENCE ELECTRODE

[75] Inventors: Nils Holmström, Järfälla; Pia Hagel, Sollentuna; Kenth Nilsson, Akersberga, all of Sweden

[73] Assignee: Pacesetter AB, Solna, Sweden

[21] Appl. No.: 748,543

[22] Filed: Nov. 13, 1996

[30] Foreign Application Priority Data

Nov. 27, 1995 [SE] Sweden .................. 9504233

[51] Int. Cl.$^6$ .................................. G01N 27/26
[52] U.S. Cl. .............. 204/403; 204/294; 204/297 R; 204/435; 128/635; 128/637; 128/642; 128/419 P; 128/899
[58] Field of Search .................. 128/635, 637, 128/642, 419 P, 899; 204/403, 435, 294, 297 R; 422/82.01, 82.03, 82.04, 82.13

[56] References Cited

U.S. PATENT DOCUMENTS

| | | | |
|---|---|---|---|
| 4,041,933 | 8/1977 | Reichenberger | 128/2 E |
| 4,125,116 | 11/1978 | Fischell | 128/404 |
| 4,589,418 | 5/1986 | Gopikanth | 128/635 |
| 4,602,637 | 7/1986 | Elmqvist et al. | 128/419 P |
| 5,230,786 | 7/1993 | Preidel | 204/435 |

FOREIGN PATENT DOCUMENTS

| | | |
|---|---|---|
| 0 453 117 | 10/1991 | European Pat. Off. |
| 0 593 990 | 4/1994 | European Pat. Off. |

OTHER PUBLICATIONS

"Oxygen Pressure as Biosenor for Rate Adaptive Cardiac Pacing," Carlsten et al., Pacing and Clinical Electrophysiology, vol. 17, no. 11, Nov. (Part II) 1994, pp. 1939–1943.

Primary Examiner—Bruce F. Bell
Attorney, Agent, or Firm—Hill, Steadman & Simpson

[57] ABSTRACT

An implantable medical device for in vivo electrochemical measurements of blood properties, such as measurements of, inter alia, oxygen pressure, glucose and pH, avoids the problem with the reference electrodes currently in use which cause inflammatory reactions of tissue, by forming the reference electrode of carbon, preferably activated pyrolytic carbon.

5 Claims, 1 Drawing Sheet

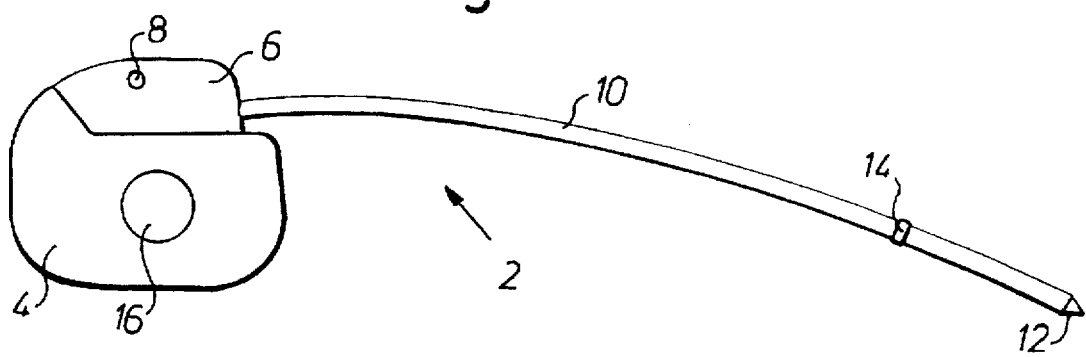
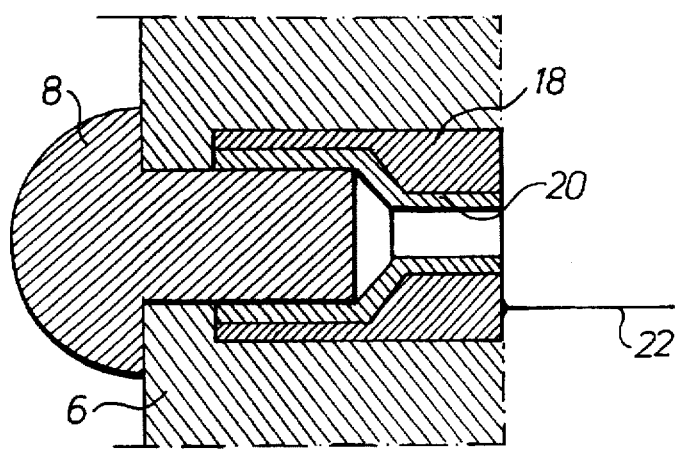

IMPLANTABLE MEDICAL DEVICE INCLUDING AN ARRANGEMENT FOR MEASURING A BLOOD PROPERTY HAVING A CARBON REFERENCE ELECTRODE

BACKGROUND OF THE INVENTION

1. Field of the Invention

The present invention relates to an implantable medical device for in-vivo electrochemical measurements of blood properties such as measurements of, inter alia, oxygen pressure, glucose and pH.

2. Description of the Prior Art

In electrochemical measurements a reference electrode is used to measure a reference potential and to relate the potentials of other electrodes to the reference potential, thereby making it possible to measure the blood property.

Electrochemical sensors and e.g. pacemakers, which are implanted in the body of a patient, require an implantable reference electrode with long-term stability. In this context, the technical literature only proposes reference electrodes made of Ag/AgCl. When these types of reference electrodes are used, however, one cannot rule out silver poisoning of the body as a result of the required long-term implantation.

The principles of an electrochemical measurement are illustrated by an example describing measurements of oxygen pressure in the article "Oxygen Pressure as Biosensor for Rate Adaptive Cardiac Pacing" by Carlsten et al: PACE 1994, 17(Pt. II): 1939–1943. The electrochemical measurement described in the article is accomplished by a sensor placed at the distal end of the pacemaker electrode lead, near the stimulation electrode, and an indifferent electrode, placed at the pacemaker housing. The oxygen molecules dissolved in the blood are chemically reduced on the surface of the sensor when its potential during a measurement pulse is forced to minus 1 volt compared to a Ag/AgCl reference electrode. In the reduction process, hydroxide ions are produced and the amount of these ions is dependent on the concentration of dissolved oxygen according to the following reactions:

At the sensor: 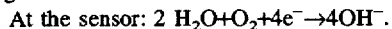 $2\ H_2O + O_2 + 4e^- \rightarrow 4OH^-$.

At the indifferent electrode: 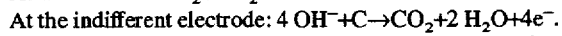 $4\ OH^- + C \rightarrow CO_2 + 2\ H_2O + 4e^-$.

The electrical current flowing into the sensor during measurement pulses is carried by hydroxide ions. This current, called oxygen current ($ipO_2$) is proportional to the amount of hydroxide ions formed on the sensor surface. The housing of the pacemaker is partially covered with carbon. When a measurement pulse is applied to the sensor the carbon coating is oxidized to produce minute amounts of carbon dioxide ($CO_2$) which is removed by the blood. The reference electrode is placed in the epoxy header of the pacemaker.

From U.S. Pat. No. 5,230,786 it is known to use a silver-chloride reference electrode used for in-vivo electrochemical measurements. To prevent silver or silver ions from diffusing into the body the silver-chloride layer is covered with a layer of, e.g., nafion. The layer of nafion is between 1 and 100 µm thick.

The thin layer of nafion, however, is sensitive to wear which can result in the silver-chloride layer coming in direct contact with blood.

Another similar solution is known from U.S. Pat. No. 4,589,418 where a silver/silver-chloride reference electrode is coated with a thin film of a silicone based polymer to reduce adverse tissue reactions.

Implanted medical devices, such as pacemakers, are often implanted in the body for a long time, up to 7–8 years, and it is of course of greatest importance that all negative tissue reactions caused by the implant are avoided. It is well known that silver/silver-chloride reference electrodes used for electrochemical measurements are not biocompatible and although several attempts have been made to reduce the inflammatory reactions sometimes resulting therefrom, the problem with the reference electrodes used today has still not been satisfactorily solved.

SUMMARY OF THE INVENTION

The above object is achieved in accordance with the principles of the present invention in an implantable medical device for electrochemical measurements of blood properties of the type described above having a reference electrode for determining a reference potential and measurement means, employing the reference electrode, for making the electrochemical measurement, the reference electrode being in contact in vivo with blood, wherein the reference electrode is comprised of carbon.

In an advantageous embodiment of the invention the type of carbon used is an activated pyrolytic carbon. This is the same material that today is used in stimulation tip electrodes. This material is well-known as being biocompatible and no adverse reactions of tissue in the long-term have been identified during animal implants. The material also has proved to have good long-term stability.

According to a further embodiment of the device according to the invention the reference electrode is fastened to a holder made of, e.g., titanium. In order to prevent oxidation between the carbon and titanium, the titanium holder is covered on the side in contact with the carbon electrode by an anti-oxidation material, e.g. titanium nitride. The carbon reference electrode in the device according to the invention is preferably fastened by glue to the holder.

DESCRIPTION OF THE DRAWINGS

FIG. 1 shows a heart stimulator comprising a medical device according to the invention.

FIG. 2 shows the reference electrode of the device according to the invention, attached to a holder.

DESCRIPTION OF THE PREFERRED EMBODIMENTS

The inventive implantable medical device is below described with reference to the accompanied figures in the form of an oxygen measuring device of a physiologically controlled heart stimulator.

In FIG. 1 an implantable heart stimulator 2 is shown with a stimulator housing 4 partially covered with carbon forming an indifferent electrode 16, a connector housing 6 where a reference electrode 8 is placed, and an electrode lead 10 connected to the connector housing 6. The electrode lead 10 includes a stimulation electrode 12 and a ring electrode 14. The ring electrode 14 is used as sensor electrode during electrochemical measurements.

As shown in FIG. 2, the carbon reference electrode 8 is attached to a holder 18 in the connector housing 6. The holder 18 is made of titanium or a non oxidizable material, e.g. gold or platinum. When using titanium for the holder 18, an anti-oxidation material 20, e.g., titanium nitride or titanium carbide, is inserted between the titanium holder 18 and the carbon reference electrode 8. The holder 18 is connected to an operational amplifier (not shown) via a connection 22.

In order to firmly attach the reference electrode 8 to the holder 18 and to prevent leakage, the reference electrode 8 is glued to the holder 18 and to the connector housing 6.

Since the pO$_2$ measurement is well described in the literature, there is no need to describe the electronics for achieving the measurement herein.

The reference electrode 8 is connected to one of the inputs of an operational amplifier (not shown) and the ring electrode 14 is connected via a resistor (not shown) to the other input. The potential on the ring electrode 14 is forced, during a short period, to minus 1 volt compared to the potential of the reference electrode 8. During this period the oxygen molecules dissolved in the blood are chemically reduced on the surface of the ring electrode 14. In the reduction process, hydroxide ions are produced and the amount of these ions are dependent on the concentration of dissolved oxygen.

The electrical current flowing to the ring electrode 14 during the measurement pulse is carried by hydroxide ions. This current, called oxygen current (ipO$_2$) is proportional to the amount of hydroxide ions formed on the ring electrode 14 surface and is thus a measure of the concentration of dissolved oxygen in blood. This current is measured and can be used for controlling a rate responsive pacemaker.

The invention has been described above applied to oxygen measurements, however, the invention can be implemented for several other measurements using electrochemical sensors, e.g. for glucose sensors or pH-sensors.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable medical device comprising:

means for making an electrochemical measurement of a blood property including a reference electrode adapted for in vivo interaction with blood; and said reference electrode consisting of activated pyrolytic carbon.

2. An implantable medical device as claimed in claim 1 wherein said means for making an electrochemical measurement includes a holder for said reference electrode, said holder consisting of titanium and having a surface in contact with said reference electrode, and an anti-oxidation material disposed between said surface and said reference electrode.

3. An implantable medical device as claimed in claim 2 wherein said anti-oxidation material comprises a material selected from the group consisting of titanium nitride and titanium carbide.

4. An implantable medical device as claimed in claim 1 wherein said means for making an electrochemical measurement includes a holder for said reference electrode, said holder consisting of gold.

5. An implantable medical device as claimed in claim 1 wherein said means for making an electrochemical measurement includes a holder for said reference electrode, said holder consisting of platinum.

* * * * *